(12) United States Patent
Nazeeruddin et al.

(10) Patent No.: US 8,980,440 B2
(45) Date of Patent: Mar. 17, 2015

(54) LIGHT-EMITTING MATERIAL

(75) Inventors: Mohammad Khaja Nazeeruddin, Ecublens (CH); Cedric Klein, Brumath (FR); Michael Graetzel, Saint Sulpice (CH)

(73) Assignee: Solvay (Societe Anonyme), Brussels (BE)

( * ) Notice: Subject to any disclaimer, the term of this patent is extended or adjusted under 35 U.S.C. 154(b) by 1073 days.

(21) Appl. No.: 12/295,933

(22) PCT Filed: Apr. 3, 2007

(86) PCT No.: PCT/EP2007/053226
§ 371 (c)(1),
(2), (4) Date: Oct. 3, 2008

(87) PCT Pub. No.: WO2007/115972
PCT Pub. Date: Oct. 18, 2007

(65) Prior Publication Data
US 2009/0115327 A1    May 7, 2009

(30) Foreign Application Priority Data
Apr. 7, 2006   (EP) .................................. 06112376

(51) Int. Cl.
*H01L 51/50* (2006.01)
*C07F 15/00* (2006.01)

(52) U.S. Cl.
CPC .......... *C07F 15/0046* (2013.01); *Y10S 428/917* (2013.01)
USPC ........ 428/690; 428/917; 428/411.1; 428/336; 548/101; 548/103

(58) Field of Classification Search
USPC ........................................................ 428/690
See application file for complete search history.

(56) References Cited

U.S. PATENT DOCUMENTS 6,245,988 B1   6/2001   Gratzel et al.
6,670,645 B2   12/2003  Grushin et al.
(Continued)

FOREIGN PATENT DOCUMENTS

JP   2003113163 A   4/2003
JP   2003113164 A   4/2003
(Continued)

OTHER PUBLICATIONS

PCT Search Report dated Aug. 1, 2007 for International Appliction No. PCT/EP2007/053226 (2 pg.).
(Continued)

*Primary Examiner* — J. L. Yang
(74) *Attorney, Agent, or Firm* — Foley & Lardner LLP (57) ABSTRACT

This invention pertains to light emitting materials comprising novel ortho-metalated transition metal complexes $[C^{\wedge}N]_2M(T)(L)$, comprising chelate dialkylamino-substituted $C^{\wedge}N$ ligands, monodentate neutral ligand (L) having $sp^2$ hybridized N atom and a monodentate anionic ligand (T) chosen among $CN^-$, $CNO^-$, $CNS^-$. It has been surprisingly found that when the metal has bound thereto in addition to substituted orthometalated ligands, both an anion chosen among cyanide, thiocyanate, cyanate, possessing strong C donor and $\pi$ acceptor properties, and a monodentate neutral ligand L, as above defined, said ligands advantageously participate in the emission process, significantly shifting emission towards higher energies (blue-shift) and enabling appreciable improvement of the emission efficiency of complexes $[C^{\wedge}N]_2M(T)(L)$.
Still objects of the invention are the use of said light emitting materials and organic light emitting device comprising said light emitting material.

17 Claims, 2 Drawing Sheets

(56) References Cited

U.S. PATENT DOCUMENTS

| | | | |
|---|---|---|---|
| 2001/0019782 A1 | 9/2001 | Igarashi et al. | |
| 2002/0182441 A1* | 12/2002 | Lamansky et al. | 428/690 |
| 2005/0048312 A1 | 3/2005 | Herron et al. | |
| 2005/0112406 A1* | 5/2005 | Han et al. | 428/690 |
| 2005/0287391 A1 | 12/2005 | Chang et al. | |

FOREIGN PATENT DOCUMENTS

| | | |
|---|---|---|
| WO | WO2006012023 A1 | 2/2006 |
| WO | WO2007004113 A2 | 1/2007 |
| WO | WO2007042474 A1 | 4/2007 |
| WO | WO2008043815 A1 | 4/2008 |

OTHER PUBLICATIONS

EPO Search Report dated Aug. 10, 2006 for European Application No. 06112376.6 (2 pg.).

U.S. Appl. No. 12/089,303 filed Apr. 4, 2008 by Sung Jin et al.—Unpublished in U.S. Published as WO 2007/042474 attached herein.

Baldo M.A., Lamansky S., Burrows P.E., Thompson M.E., Forrest S.R., Very high-efficiency green organic light-emitting devices based on electrophosphorescence, Appl. phys. lett.. 1999, vol. 75, p. 4-6 (3 pg.).

Lee, Chang-Lyoul, et al. Polymer-based blue electrophosphorescent light-emitting diodes using a bisorthometalated Ir (III) complex as triplet emitter. Chemistry of Materials. 2004, vol. 16, No. 23, p. 4642-4646 (5 pg.).

Nazeeruddin, Md. K., et al. Highly phosphorescent iridium complexes and their application in organic light-emitting devices. J. Am. Chem. Soc.. 2003, vol. 125, No. 29, p. 8790-8797 (8 pg.).

Lohse, Olivier; Thevenin, Philippe; Waldvogel, Erwin. The Palladium Catalyzed Suzuki Coupling of 2- and 4-chloropyridines. Syn. Lett. 1999, No. 1, p. 45-48 (4 pg.).

S. Sprouse, K. A. King, P. J. Spellane, R. J. Watts, Photophysical effects of metal-carbon .sigma. bonds in ortho-metalated complexes of iridium(III) and rhodium(III). J. Am. Chem. Soc., 1984, 106, 6647-6653 (7 pg.).

Sergey Lamansky, Peter Djurovich, Drew Murphy, Feras Abdel-Razzaq, Raymond Kwong, Irina Tsyba, Manfred Bortz, Becky Mui, Robert Bau, and Mark E. Thompson, Synthesis and Characterization of Phosphorescent Cyclometalated Iridium Complexes, Inorg. Chem., 2001, 40(7), 1704-1711 (8 pg.).

Sergey Lamansky, Peter Djurovich, Drew Murphy, Feras Abdel-Razzaq, Hae-Eun Lee, Chihaya Adachi, Paul E. Burrows, Stephen R. Forrest, and Mark E. Thompson, Highly Phosphorescent Bis-Cyclometalated Iridium Complexes: Synthesis, Photophysical Characterization, and Use in Organic Light Emitting Diodes, J. Am. Chem. Soc., 2001, 123(18), 4304-4312 (9 pg.).

Cuperly, D.;.Gros, P.; Fort, Y., First Direct C-2-Lithiation of 4-DMAP. Convenient Access to Reactive Functional Derivatives and Ligands. J. Org. Chem. 2002, 67, 238-241 (4 pg.).

\* cited by examiner

LIGHT-EMITTING MATERIAL

CROSS-REFERENCE TO RELATED APPLICATIONS

This application is a U.S. national stage application under 35 U.S.C. §371 of International Application No. PCT/EP2007/053226, filed Apr. 3, 2007, which claims priority to European Application No. 06112376.6, filed Apr. 7, 2006, all of these applications being herein incorporated by reference in their entirety for all purposes.

TECHNICAL FIELD

This invention relates to a light-emitting material, to the use of said material and to light-emitting device capable of converting electric energy to light.

BACKGROUND ART

Today, various display devices have been under active study and development, in particular those based on electroluminescence (EL) from organic materials.

In the contrast to photoluminescence, i.e. the light emission from an active material as a consequence of optical absorption and relaxation by radiative decay of an excited state, electroluminescence (EL) is a non-thermal generation of light resulting from the application of an electric field to a substrate. In this latter case, excitation is accomplished by recombination of charge carriers of contrary signs (electrons and holes) injected into an organic semiconductor in the presence of an external circuit.

A simple prototype of an organic light-emitting diode (OLED), i.e. a single layer OLED, is typically composed of a thin film of the active organic material which is sandwiched between to electrodes, one of which needs to be semitransparent in order to observe light emission from the organic layer; usually an indium tin oxide (ITO)-coated glass substrate is used as anode.

If an external voltage is applied to the to electrodes, charge carriers, i.e. holes, at the anode and electrons at the cathode are injected to the organic layer beyond a specific threshold voltage depending on the organic material applied. In the presence of an electric field charge carriers move through the active layer and are non-radiatively discharged when they reach the oppositely charged electrode. However, if a hole and an electron encounter one another while drifting through the organic layer, excited singlet (anti-symmetric) and triplet (symmetric) states, so-called excitons, are formed. Light is thus generated in the organic material from the decay of molecular excited states (or excitons). For every three triplet excitons that are formed by electrical excitation in an OLED, only one symmetric state (singlet) exciton is created.

Many organic materials exhibit fluorescence (i.e. luminescence from a symmetry-allowed process) from singlet excitons: since this process occurs between states of same symmetry it may be very efficient. On the contrary, if the symmetry of an exciton is different from the one of the ground state, then the radiative relaxation of the exciton is disallowed and luminescence will be slow and inefficient. Because the ground state is usually anti-symmetric, decay from a triplet breaks symmetry: the process is thus disallowed and efficiency of EL is very low. Thus the energy contained in the triplet states is mostly wasted.

Luminescence from a symmetry-disallowed process is known as phosphorescence. Characteristically, phosphorescence may persist for up to several seconds after excitation due to the low probability of the transition, in contrast to fluorescence which originates in the rapid decay.

However, only a few organic materials have been identified which show efficient room temperature phosphorescence from triplets.

Successful utilization of phosphorescent materials holds enormous promises for organic electroluminescent devices. For example, an advantage of utilizing phosphorescent materials is that all excitons (formed by combination of holes and electrons in an EL), which are (in part) triplet-based in phosphorescent devices, may participate in energy transfer and luminescence. This can be achieved either via phosphorescence emission itself, or using phosphorescent materials for improving efficiency of the fluorescence process as a phosphorescent host or a dopant in a fluorescent guest, with phosphorescence from a triplet state of the host enabling energy transfer from a triplet state of the host to a singlet state of the guest.

In each case, it is important that the light emitting material provides electroluminescence emission in a relatively narrow band centered near selected spectral regions, which correspond to one of the three primary colours, red, green and blue, so that they may be used as a coloured layer in an OLED.

As a means for improving the properties of light-emitting devices, there has been reported a green light-emitting device utilizing the emission from ortho-metalated iridium complex Non Patent Citation 0001: (Ir(ppy)3: tris-ortho-metalated complex of iridium (III) with 2-phenylpyridine (ppy). *Appl. phys. lett.*, 1999 vol. 75, p. 4. ISSN 0003-6951.

Thus,

Non Patent Citation 0002: LEE, Chang-Lyoul. Polymer-based blue electrophosphorescent light-emitting diodes using a bisorthometalated Ir(III) complex as triplet emitter. *Chemistry of Materials*, 2004 vol. 16, no. 23, p. 4642-4646.

discloses bis-orthometalated Iridium complexes bearing as ancillary ligands a combination of a cyano anion with a monodentate phosphorous donor, like notably Ir(ppy)$_2$ P(n-Bu)$_3$CN complex (ppy=2-phenylpyridine), whose structure is depicted here below:

Non Patent Citation 0003: NAZEERUDDIN, Md. K. Highly phosphorescent iridium complexes and their application in organic light-emitting devices. *J. Am. Chem. Soc.*, 2003 vol. 125, no. 29, p. 8790-8797. ISSN 0002-7863.

discloses anionic mixed ligand Iridium (+111) complexes obtained by reaction of [IR(ppy)$_2$(Cl)]$_2$ (ppy=2-phenylpyridine) with tetraalkylammonium cyanide, thiocyanate or cyanate, whose structures are depicted here below, exhibiting high phosphorescence quantum yields:

Patent Citation 0001: U.S. Pat. No. 6,245,988 B (ECOLE POLYTECHNIQUE FEDERALE DE LAUSANNE). 2001 Jun. 12.

discloses photosensitizer complexes useful in photovoltaic cells complying with formulae (Ia) and (Ib) here below:

$$MX_3L_t \quad (Ia)$$

$$MXYL_t \quad (Ib)$$

wherein M is a transition metal chosen among Ru, Os, Fe, Re and Tc, X is a co-ligand independently selected from $NCS^-$, $Cl^-$, $Br^-$, $I^-$, $CN^-$, $NCO^-$, $H_2O$, $NCH^{2-}$; pyridine unsubstituted or substituted by at least one group selected from vinyl, primary, secondary or tertiary amine, OH and $C_{1\text{-}30}$ alkyl, Y is a bidentate N☐N ligand chosen among substituted or unsubstituted bipyridine or o-phenantroline, and L, is a tridentate N☐N☐N ligand comprising heterocycles such as pyridine and/or triazole.

Patent Citation 0002: U.S. Pat. No. 6,670,645 B (DUPONT DE NEMOURS. 2003 Dec. 30.

discloses electroluminescent Ir(III) compounds comprising substituted 2-phenylpyridines, phenylpyrimidines, and phenylquinolines and, optionally, ancillary monodentate ligands such as chloride and nitrate anions, phosphines, isonitriles, carbon monoxide, mono-amines.

Patent Citation 0003: US 20050048312 A (DU PONT DE NEMOURS). 2005 May 3.

discloses electroluminescent complexes comprising, inter alia, additional ligands such as permutations of amines, phosphines, alkoxydes, halides, hydrides or orthometalated aryl groups.

Patent Citation 0004: WO WO 2006/012023 A (EASTMAN KODAK COMPANY). 2006 Feb. 2.

discloses a process for forming a tris-cyclometallated iridium or rhodium complex comprises reacting in the presence of a solvent: a) a bis-cyclometallated complex (A) comprising an Ir (III) or Rh (III) metal, two bidentate ligands, two monodentate ligands and a counterion, and b) a heterocyclic compound capable of forming an organometallic cyclometallated complex. Among bis-cyclometallated complexes (A), mention is notably made of ionic Ir complexes bearing either nitrile ligands (cationic complexes A1 to A3 here below) or thiocyanate anions (anionic ligands A4 and A5):

(A1)

(A2)

(A3)

(A4)

(A5)

However, since the foregoing light-emitting materials of the prior art do not display pure colours, i.e. their emission bands, generally limited to green, are not centered near selected spectral regions, which correspond to one of the three primary colours, red, green and blue, the range within they can be applied as OLED active compound is narrow. It has thus been desired to develop light-emitting materials capable of emitting light having other colours, especially in the blue region. Triple emissive blue has been recognized in the art as difficult to attain due to the high energy of the emissive state.

Efficient long-lived blue-light emitters with good colour coordinates are a recognized current shortfall in the field of organic electroluminescent devices.

Patent Citation 0005: US 2005/0112406 2005 May 26.

discloses organometallic complexes suitably used for forming an organic layer of an electroluminescence device, providing maximum emission in the wavelength range of 400 to 650 nm, complying with formula here below:

wherein M is a metal chosen among, inter alia, Ir; CyN represents a heterocyclic group containing nitrogen bonded to M; CyC is a carbocyclic group containing carbon bonded to M; CyN-CyC being a cyclometalating ligand bonded to M; A is a ligand containing nitrogen bonded to M; X is a monoanionic monodentate ligand chosen among inter alia, CN, SCN, OCN. Said document discloses, in particular, complexes bearing two substituted phenylpyridine ligands, an imidazoyl ligand and a cyanide, thiocyanate, or cyanate anion.

Patent Citation 0006: US 2001019782 (FUJI PHOTO FILM). 2001 Sep. 6.

discloses light emitting iridium complexes bearing ortho-metalated ligands. Among suitable complexes, mention is notably made of compound complying with formula hereinafter:

comprising tow phenylpyridine orthometalated ligands, a pyridine ligand and a cyanide anion.

Patent Citation 0007: US 2002182441 (TRUSTEE OF PRINCETON UNIVERSITY). 2002 Dec. 5.

discloses emissive phosphorescent organometallic compounds producing electroluminescence, particularly in the blue region of the visible spectrum. In particular said document discloses a compound of formula:

comprising two fluorine-substituted phenylpyridine ligands, a pyridine ligand and a cyanide anion.

DISCLOSURE OF INVENTION

It is thus a first object of the invention to provide a light emitting material comprising a neutral ortho-metalated complex comprising ancillary ligands as detailed here below.

Still object of the invention are the use of said light emitting material and organic light emitting device comprising said light emitting material.

BRIEF DESCRIPTION OF THE DRAWINGS

FIG. 0001 depicts an OLED embodiment with a multilayer structure.

FIG. 0002 depicts the emission spectra registered from a complex (XIV) solution in dichloromethane at 273 K by excitation at 380 nm; the abscissa stand for the wavelength in nm and the ordinate stands for emission intensity (cps).

FIG. 0003 shows the adsorption spectra registered from a complex (XIV) solution in dichloromethane at 273 K; the abscissa stand for the wavelength in nm and the ordinate stands for adsorption (OD).

FIG. 0004 depicts the emission spectra registered from solutions of complex (XIV), complex (XIX) and comparative complex (XXIX) in dichloromethane.

DETAILED DESCRIPTION OF THE PREFERRED EMBODIMENTS

A first object of the invention is to provide for a light emitting material comprising a neutral complex of formula (I):

wherein:

M represents a transition metal of atomic number of at least 40, preferably of groups 8 to 12, more preferably Ir or Pt, most preferably Ir;

$E_1$ represents a non metallic atom group required to form a 5- or 6-membered aromatic or heteroaromatic ring optionally condensed with additional aromatic moieties or non aromatic cycles, said ring optionally having one or more substituents, optionally forming a condensed structure with the ring comprising $E_2$, said ring coordinating to the metal M via a $sp^2$ hybridized carbon;

$E_2$ represents a non metallic atom group required to form a 5- or 6-membered heteroaromatic ring optionally condensed with additional aromatic moieties or non aromatic cycles, said ring optionally having one or more substituents, optionally forming a condensed structure with the ring comprising $E_1$, said ring coordinating to the metal M via a $sp^2$ hybridized nitrogen;

T is a monodentate anionic ligand chosen among cyanide (CN), thiocyanate (NCS) and cyanate (NCO); preferably T is a cyanide (CN);

L is a monodentate neutral ligand, coordinating to the metal M through a $sp^2$ or $sp^3$ hybridized nitrogen atom, preferably through a $sp^2$ hybridized nitrogen atom;

$R^x$ and $R^y$ equal or different at each occurrence, are independently chosen among $C_1$-$C_6$ alkyl, fluoro- or perfluoroalkyl groups, e.g. —$CH_3$, -$nC_4H_9$, -$iC_3H_7$, —$CF_3$, —$C_2F_5$, —$C_3F_7$ or $C_1$-$C_6$ alkyl, fluoro- or perfluoroalkyl groups having one or more ether groups; preferably $R^x$ and $R^y$ are independently chosen among $C_1$-$C_6$ alkyl groups; more preferably $R^x$ and $R^y$ being selected from methyl, ethyl, n-propyl, i-propyl, n-butyl groups.

w is an integer between 1 and 4.

The two chelating monoanionic ligands bound to the metal as above specified in formula (I), comprising $E_1$ and $E_2$ moieties, are generally denoted as orthometalated ligands (CAN ligands, hereinafter).

It has been surprisingly found that when the metal has bound thereto both an anion chosen among cyanide, thiocyanate, and cyanate, possessing strong a donor and n acceptor properties, and a monodentate neutral ligand L, as above defined, when combined with orthometalated ligands CAN comprising at least one dialkylamino group —$NR_xR_y$, said ligands advantageously cooperate in the emission process, significantly shifting emission towards higher energies (blueshift) and enabling appreciable improvement of the emission efficiency of complexes $[C\hat{}N]_2M(T)L$.

Moreover, by means of the proper combination of the orthometalated ligands, of the monodentate neutral ligand (L) and of the monodentate anionic ligand (T) as above specified, it is advantageously possible to obtain light emitting materials comprising $[C\hat{}N]_2M(T)(L)$ complexes of formula (I) here above, having maximum emission between 430 nm and 500 nm, thus corresponding to a blue emission.

Neutral complexes complying with formula (I) here above are also preferred over ionic (cationic or anionic) complexes because they are generally less sensitive to moisture and they can be advantageously sublimated for throughout purification.

Preferably, the light emitting material of the invention comprises a neutral complex of formula (II):

(II)

wherein:

$R_x$, $R_y$, w, L and T have the same meaning as above defined;

X is a group chosen among the group consisting of —CH=CH—, —CR=CH—, —CR=CR—, N—H, N—$R^1$, O, S or Se; preferably X is a group selected among —CH=CH—, —CR=CH— or S; most preferably X is —CH=CH—;

Y is a group chosen among the group consisting of —CH=CH—, —CR=CH—, —CR=CR—, N—H, N—$R^1$, O, S or Se; preferably Y is a group selected among —CH=CH—, —CR=CH— or S; most preferably Y is —CH=CH—;

$R_1$, the same or different at each occurrence, is independently an aliphatic or aromatic hydrocarbon radical having from 1 to 20 carbon atoms;

$R_A$ and $R_B$, equal or different each other and at each occurrence are independently selected among —F, —Cl, —Br, —$NO_2$, —CN; a straight-chain or branched or cyclic alkyl or alkoxy group having from 1 to 20 carbon atoms, in each of which one or more nonadjacent —$CH_2$— groups may be replaced by —O—, —S—, —$NR^1$—, or —$CONR^2$—, and in each of which one or more hydrogen atoms may be replaced by F; an aryl or heteroaryl group having from 4 to 14 carbon atoms which may be substituted by one or more nonaromatic radicals; and a plurality of substituents $R_A$ and/or $R_B$, either on the same ring or on the two different rings, may in turn together form a further mono- or polycyclic ring system, optionally aromatic; preferably $R_A$ and/or $R_B$ are fluorine group(s) (—F) and/or alkoxy group(s) having from 1 to 20 carbon atoms;

a is an integer from 0 to 4;

b is an integer from 0 to 4.

Non limitative examples of monodentate neutral ligands (L) coordinating to the metal through a $sp^3$ hybridizer nitrogen atom are notably those encompassed by the following formula:

wherein $R_{N1}$, $R_{N2}$, $R_{N3}$, equal or different each other, are independently chosen among $C_{1-20}$ hydrocarbon group, e.g. aliphatic and/or aromatic, linear or branched, optionally substituted.

Preferred monodentate neutral ligands (L) coordinating to the metal through a $sp^3$ hybridizer nitrogen atom are those complying with formula here below:

wherein:

$R_{N1}$, $R_{N2}$ have the same meaning as above defined, preferably $R_{N1}$, $R_{N2}$ being independently chosen among $C_{1-20}$ aliphatic group, linear or branched, optionally substituted, $R_{Ar1}$ is a substitutent optionally comprising heteroatoms, e.g. nitrogen or oxygen, like notably a $C_{1-6}$ alkoxy group, a $C_{1-6}$ dialkyl amino group and the like; preferably $R_{Ar1}$ being a methoxy group;

$n_{Ar}$ being an integer from 0 to 5, preferably from 1 to 3, more preferably 2.

Preferably the monodentate neutral ligand (L) coordinates to the metal through a $sp^2$ hybridizer nitrogen atom. Monodentate neutral ligand (L) coordinating to the metal through a $sp^2$ hybridizer nitrogen atom comprises advantageously at least one imine group.

Preferably, the monodentate neutral ligand (L) is selected from the structures represented by following formulae (III) to (X) or tautomers thereof:

wherein:
J is a group chosen among the group consisting of —CH=CH—, —CR=CH—, —CR=CR—, N—H, N—R$^1$, O, S or Se;
G is a group chosen among the group consisting —CH=CH—, —CR=CH—, —CR'=CR'—, N—H, N—R$^1$, —CH=N—, —CR'=N—;
Z is a substituent selected from the group consisting of halogens, such as —Cl, —F, —Br; —OR$_0$; —SR$_0$; —N(R$_0$)$_2$; —P(OR$_0$)$_2$ and —P(R$_0$)$_2$; wherein R$_0$ is a C$_1$-C$_6$ alkyl, fluoro- or perfluoroalkyl group, e.g. —CH$_3$, -nC$_4$H$_9$, -iC$_3$H$_7$, —CF$_3$, —C$_2$F$_5$, —C$_3$F$_7$ or a C$_1$-C$_6$ alkyl, fluoro- or perfluoroalkyl group having one or more ether groups, e.g. —CH$_2$—(CH$_2$—O—CH$_2$)$_n$—CH$_3$, —CH$_2$—[CH$_2$(CH$_3$)—O—CH$_2$]$_n$—CH$_3$, —(CF$_2$O), —C$_2$F$_5$, with n being an integer from 1 to 8;
R', R*, R¤, the same or different each other at each occurrence, represent F, Cl, Br, NO$_2$, CN, a straight-chain or branched or cyclic alkyl or alkoxy group having from 1 to 20 carbon atoms, in each of which one or more nonadjacent —CH$_2$— groups may be replaced by —O—, —S—, —NR$^1$—, or —CONR$^2$—, and in each of which one or more hydrogen atoms may be replaced by F; or an aryl or heteroaryl group having from 4 to 14 carbon atoms which may be substituted by one or more non aromatic radicals; and a plurality of substituents R', R*, or R¤, either on the same ring or on the two different rings, may in turn together form a further mono- or polycyclic ring system, optionally aromatic;
R", R$^1$, R$^2$, the same or different at each occurrence, are each H or an aliphatic or aromatic hydrocarbon radical having from 1 to 20 carbon atoms;
d is an integer from 0 to 3;
c is an integer from 0 to 3.

To the purpose of the invention, the term tautomer is intended to denote one of two or more structural isomer that exist in equilibrium and are readily converted from one isomeric form to another, by, for instance, simultaneous shift of electrons and/or of a hydrogen atom.

Light emitting materials particularly suitable for the invention comprise a neutral complex of formula (XI) here below:

wherein:
T, Y, X, G, R$_A$, R$_B$, R$^x$, R$^y$, a, b, and w have the same meaning as above defined, and w' is an integer between 0 and 3.

Light emitting materials which gave good results are those comprising a neutral complex of formula (XII):

wherein:
R$^x$, R$^y$, w and w' have the same meaning as above defined;
R$_M$, equal or different at each occurrence, is independently selected from —F and alkoxy group having from 1 to 20 carbon atoms; and
m is an integer between 1 and 4, preferably between 1 and 3.

Complexes complying with formula (XII) here above, thanks to the substitution of one or more hydrogen atoms with fluorine atoms or alkoxy groups advantageously exhibit improved chemical and thermal stability, which enable handling and treating them in further processing technologies without any risk of decomposition nor degradation.

Very good results were obtained with light emitting materials comprising a neutral complex of formula (XIII) to (XVII):

(XIII)

(XIV)

(XV)

(XVI)

(XVII)

Also light emitting materials comprising a neutral complex of formula (XVIII) to (XXII) gave very satisfactory results:

(XVIII)

(XIX)

(XX)

(XXI)

(XXII)

A complex which gave excellent result is complex of here below:

(XIV)

Neutral complex of formula (XIV) comprising dimethylamino-substituted orthometalated ligands and a dimethylamino-substituted pyridine and a cyano anion as ancillary ligands are particularly advantageous for the purposes of the invention because of their emission in the blue region with high colour purity.

Another complex which gave very satisfactory results is complex of formula (XIX) here below:

(XIX)

The synthesis of complexes of formula (I) here above, i.e. metal complex comprising two orthometalated ligands (CAN ligands), an anionic monodentate ligand (T) and a neutral monodentate ligand (L), as above specified can be accomplished by any known method. Details of synthetic methods suitable for the preparation of complexes of formula (I) here above are notably disclosed in "Inorg. Chem.", No. 30, pag. 1685 (1991); "Inorg. Chem.", No. 27, pag. 3464 (1988); "Inorg. Chem.", No. 33, pag. 545 (1994); "Inorg. Chem. Acta", No. 181, pag. 245 (1991), "J. Organomet. Chem.", No. 35, pag. 293 (1987, "J. Am. Chem. Soc.", No. 107, pag. 1431 (1985).

Generally, complexes complying with formula (I) here above can be prepared according to the following reaction scheme:

Acid forms of the orthometalated ligands (H—C^N) and of ancillary ligands (L-H) can be either commercially available or easily synthesized by well-known organic synthesis reaction pathways, well-known to those skilled in the art.

In particular, orthometalated ligands (H—C^N) can be notably prepared in good to excellent yield, using the Suzuki coupling or the substituted 2-chloropyridine, 2-chloropirimidine, 2-chloroquinoline or other N-heteroaromatic compound with corresponding arylboronic acids as described in Non Patent Citation 0004: LOHSE, Olivier. The Palladium Catalyzed Suzuki Coupling of 2- and 4-chloropyridines. *Syn. Lett.*, 1999 no. 1, p. 15-18.

and in

Patent Citation 0008: U.S. Pat. No. 6,670,645 (DU PONT DE NEMOURS. 2003 Dec. 30.

Synthetic methods particularly adapted to the preparation of fluorinated orthometalated ligands (H—C^N) are described in Patent Citation 0009: JP 2003113164 A (MITSUBISHI MATERIALS CORP). 2003 Apr. 18.

and in

Patent Citation 0010: JP 2003113163 A (MITSUBISHI MATERIALS CORP). 2003 Apr. 18.

Should the transition metal be iridium, trihalogenated iridium (III) compounds such as $IrCl_3 \cdot H_2O$, hexahalogenated Iridium (III) compounds, such as $M_3IrX_6$, wherein X. is a halogen, preferably Cl and M. is an alkaline metal, preferably K, and hexahalogenated iridium (IV) compounds such as $M_2IrX_6$, wherein X. is a halogen, preferably Cl and M. is an alkaline metal, preferably K (Ir halogenated precursors, hereinafter) can be used as starting materials to synthesize the complexes of formula (I), as above described.

$[C^{\wedge}N]_2Ir(\mu-X.)_2Ir[C^{\wedge}N]_2$ complexes (compound XXV, wherein M=Ir), with X. being a halogen, preferably Cl, can be thus prepared from said Ir halogenated precursors and the appropriate orthometalated ligand by literature procedures (S. Sprouse, K. A. King P. J. Spellane, R. J. Watts, J. Am. Chem. Sic., 1984, 106, 6647-6653; M. E. Thompson et al., Inorg. Chem., 2001, 40(7), 1704; M. E. Thompson et al., J. Am. Chem. Soc., 2001, 123(11, 4304-4312).

Reaction is advantageously carried out using an excess of the neutral form of the orthometalated ligand (H—C^N); high-boiling temperature solvent are preferred.

To the purpose of the invention, the term high-boiling temperature solvent is intended to denote a solvent having a boiling point of at least 80° C., preferably of at least 85° C., more preferably of at least 90° C. Suitable solvents are for instance ethoxyethanol, glycerol, dimethylformamide (DMF), N-methylpirrolidone (NMP), dimethylsulfoxide (DMSO), and the like; said solvents can be used as such or in admixture with water.

Optionally reaction can be carried out in the presence of a suitable Brønsted base, such as metal carbonates, in particular potassium carbonate ($K_2CO_3$), metal hydrides, in particular sodium hydride (NaH), metal ethoxide or metal methoxide, in particular $NaOCH_3$, $NaOC_2H_5$, alkylammonium hydroxides, in particular tetramethylammonium hydroxide, or imidazolium hydroxides.

A first nucleophilic substitution at the metal atom with a suitable ligand L, as above defined to form corresponding [C^N]$_2$Ir(L)X (formula XXVI, here above) is advantageously carried out by contacting roughly stoichiometric amount of ligand L with bridged intermediate (XXV) in a suitable solvent.

Polar aprotic solvents are generally preferred for this reaction; a solvent which gave particularly good results is methylene dichloride ($CH_2Cl_2$).

[C^N]$_2$M(T)(L) complexes can be finally obtained by reaction of said [C^N]$_2$Ir(L)X (formula XXVII) with a suitable salt of anionic ligand T. Preferred salts of anionic ligand T are notably ammonium salts of formula $(R_N^1 R_N^2 R_N^3 R_N^4)_4 N^+ T^-$ wherein:

each of $R_N^1$, $R_N^2$, $R_N^3$, and $R_N^4$, equal or different each other, is independently chosen among hydrogen and $C_{1-20}$ alkyl group;

T is a monodentate anionic ligand chosen among cyanide (CN), thiocyanate (NCS) and cyanate (NCO); preferably T is a cyanide (CN)

More preferably, the salt is a tetralkylammonium salt of formula:

$(R_P)_4 N^+ T^-$ wherein $R_P$ is a $C_{1-6}$ alkyl group, preferably a n-butyl group.

The reaction is preferably carried out in a polar aprotic solvent. A solvent which gave particularly good results is methylene dichloride ($CH_2Cl_2$).

The present invention is also directed to the use of the light emitting material as above described in the emitting layer of an organic light emitting device (OLED).

Furthermore, the present invention is directed to the use of the light emitting material as above described as dopant in a host layer, functioning as an emissive layer in an organic light emitting device.

Should the light emitting material used as dopant in a host layer, it is generally used in an amount of at least 1% wt, preferably of at least 3% wt, more preferably of least 5% wt with respect to the total weight of the host and the dopant and generally of at most 25% wt, preferably at most 20% wt, more preferably at most 15% wt.

The present invention is also directed to an organic light emitting device (OLED) comprising an emissive layer (EML), said emissive layer comprising the light emitting material as above described, optionally with a host material (wherein the light emitting material as above described is preferably present as a dopant), said host material being notably adapted to luminesce when a voltage is applied across the device structure.

The OLED generally comprises:
a glass substrate;
an anode, generally transparent anode, such as an indium-tin oxide (ITO) anode;
a hole transporting layer (HTL);
an emissive layer (EML);
an electron transporting layer (ETL);
a cathode, generally a metallic cathode, such as an Al layer.

For a hole conducting emissive layer, one may have an exciton blocking layer, notably a hole blocking layer (HBL) between the emissive layer and the electron transporting layer. For an electron conducting emissive layer, one may have an exciton blocking layer, notably an electron blocking layer (EBL) between the emissive layer and the hole transporting layer. The emissive layer may be equal to the hole transporting layer (in which case the exciton blocking layer is near or at the anode) or to the electron transporting layer (in which case the exciton blocking layer is near or at the cathode).

The emissive layer may be formed with a host material in which the light emitting material as above described resides as a guest or the emissive layer may consist essentially of the light emitting material as above described itself. In the former case, the host material may be a hole-transporting material selected from the group of substituted tri-aryl amines. Preferably, the emissive layer is formed with a host material in which the light emitting material resides as a guest. The host material may be an electron-transporting material selected from the group of metal quinoxolates (e.g. aluminium quinolate (Alq$_3$), lithium quinolate (Liq)), oxadiazoles and triazoles. An example of a host material is 4,4'-N,N'-dicarbazole-biphenyl ["CBP"], which has the formula:

CBP

Optionally, the emissive layer may also contain a polarization molecule, present as a dopant in said host material and having a dipole moment, that generally affects the wavelength of light emitted when said light emitting material as above described used as dopant, luminesces.

A layer formed of an electron transporting material is advantageously used to transport electrons into the emissive layer comprising the light emitting material and the (optional) host material. The electron transporting material may be an electron-transporting matrix selected from the group of metal quinoxolates (e.g. Alq$_3$, Liq), oxadiazoles and triazoles. An example of an electron transporting material is tris-(8-hydroxyquinoline)aluminum of formula ["Alq$_3$"]:

Alq$_3$

A layer formed of a hole transporting material is advantageously used to transport holes into the emissive layer comprising the light emitting material as above described and the (optional) host material. An example of a hole transporting material is 4,4'-bis[N-(1-naphthyl)-N-phenylamino]biphenyl ["α-NPD"].

α-NPD

The use of an exciton blocking layer ("barrier layer") to confine excitons within the luminescent layer ("luminescent zone") is greatly preferred. For a hole-transporting host, the blocking layer may be placed between the emissive layer and the electron transport layer. An example of a material for such a barrier layer is 2,9-dimethyl-4,7-diphenyl-1,10-phenanthroline (also called bathocuproine or "BCP"), which has the formula

BCP

Figure 0001:
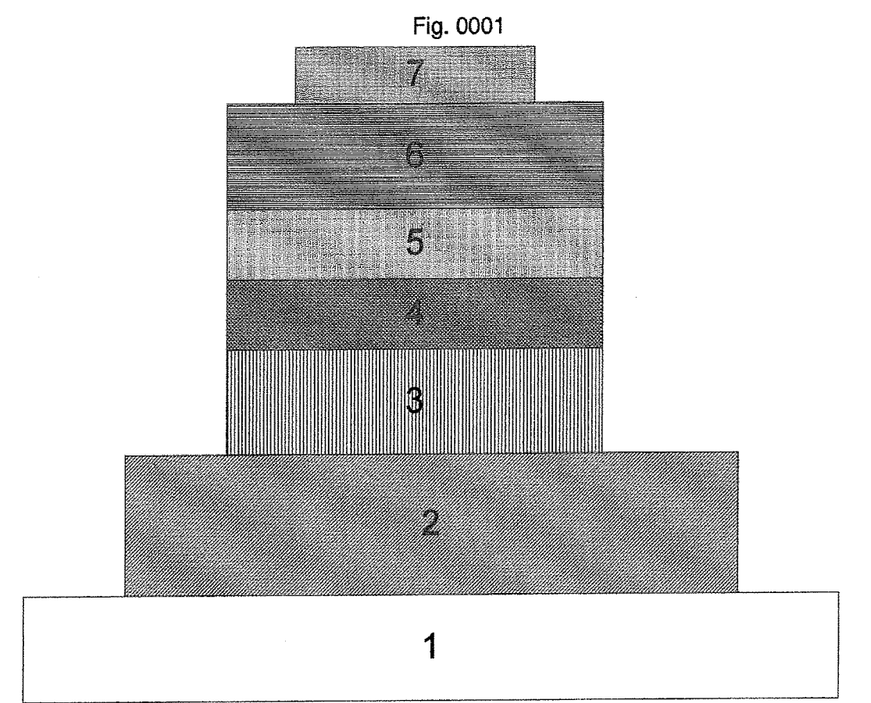

The OLED has preferably a multilayer structure, as depicted in FIG. 0001, wherein 1 is a glass substrate, 2 is an ITO layer, 3 is a HTL layer comprising α-NPD, 4 is an EML comprising CBP as host material and the light emitting material as above defined as dopant in an amount of about 8% wt with respect to the total weight of host plus dopant; 5 is a HBL comprising BCP; 6 is an ETL comprising Alq$_3$; 7 is an Al layer cathode.

EXAMPLES

UV-VIS Measurements: UV-VIS spectra were recorded in a 1 cm path length quartz cell on a Cary 5 spectrophotometer. Emission spectra were recorded on a Spex Fluorolog 112 using a 90° optical geometry. The emitted light was detected with a Hamamatsu R2658 photomultiplier operated in single photon counting mode. The emission spectra were photometrically corrected using a NBS calibrated 200 W tungsten lamp as reference source. The absorption and the emission spectra were obtained by dissolving the solids in dichloromethane solvent and the concentrations were in the range of $5\times10^{-6}$ to $1\times10^{-5}$ M. All the emission spectra were obtained by exciting at 380 nm and the typical concentrations were $1\times10^5$ M.

Synthesis of 2-iodo-4-dimethylaminopyridine

BF$_3$.Et$_2$O (8.4 g 59 mmol) was added dropwise to a solution of 4-dimethylaminopyridine (6 g 49 mmol) in dry THF (250 ml) at 0° C. The resulting mixture was stirred 1 hour at 0° C. under nitrogen. Temperature was cooled down to −78° C. and BuLi (1.6 M in hexane, 46 ml, 74 mmol) was added dropwise. The resulting mixture was stirred for 1 hour at −78° C. and a solution of I$_2$ (18.7 g, 74 mmol) in dry THF (50 ml) was added dropwise. The resulting mixture was stirred at −78° C. for 2 hours and allowed to warm to room temperature (2 hours). THF was evaporated and a saturated Na$_2$S$_2$O$_5$ solution was added. The resulting slurry was extracted with EtOAc (5×150 ml). The combined organic fractions were successively washed with saturated Na$_2$S$_2$O$_5$ (50 ml), brine (50 ml), dried over MgSO$_4$, filtered and evaporated to dryness. The resulting residue was purified by chromatography column (SiO$_2$, EtOAc/petroleum ether, 1/1) to afford 7 g (57%) of the desired compound as colourless oil which solidify upon standing.

$^1$H and $^{13}$C NMR were in agreement with those reported in the literature (Cuperly, D.; Gros, P.; Fort, Y. *J. Org. Chem.* 2002, 67, 238-241).

Synthesis of 2-(2,4-difluorophenyl)-4-dimethylaminopyridine

A mixture of 2-iodo-4-dimethylaminopyridine (3 g, 12 mmol), 2,4-difluorophenylboronic acid (2.3 g, 14.5 mmol) and K$_2$CO$_3$ (6 g 43.5 mmol) in toluene (60 ml) and water (10 ml) were degassed with nitrogen for 15 minutes. Pd(PPh$_3$)$_4$ (800 mg, 0.66 mmol) was added and the resulting mixture was heated to 90° C. for 48 hours under nitrogen. After being cooled to room temperature, the aqueous phase was separated and extracted with EtOAc (3×100 ml). The combined organic fractions were washed with brine, dried over MgSO$_4$, filtered and evaporated. To further purify the compound the so-obtained oil was dissolved in Et$_2$O and extracted with 10% HCl solution (3×50 ml). The combined aqueous fractions were washed with Et$_2$O (2×100 ml) and neutralized with concentrated NaOH aqueous solution. The resulting mixture was extracted with EtOAc (4×100 ml), the combined organic fractions were washed with brine (50 ml), dried over MgSO4, filtered and evaporated to dryness. The crude compound was purified by column chromatography (SiO$_2$, CHCl$_3$ then CHCl$_3$/MeOH, 97/3) to afford 2.2 g (78%) of the titled compound as slightly yellow oil which solidified upon standing.

$^1$H-NMR (CDCl$_3$, 298K, 200 MHz, δ ppm) 3.05 (s, 6H), 6.49 (dd, J=2.5 and 6 Hz, 1H), 6.92 (m, 3H), 7.94 (m, 1H), 8.33 (d, J=6 Hz, 1H).

Synthesis of [(2-(2,4-difluorophenyl)-4-dimethylaminopyridine)$_2$IrCl]$_2$

IrCl$_3$.3H$_2$O and 2.5 equivalents of 2-(2,4-difluorophenyl)-4-dimethylaminopyridine were heated at 110° C. in a mixture of 2-ethoxyethanol and water (3/1, v/v) overnight under nitrogen. After being cooled to room temperature, the resulting precipitate was filtered off, successively washed with methanol than Et$_2$O and finally dried to afford the desired dimer. Because of the low solubility of this compound, its $^1$H-NMR was recorded in DMSO-d$^6$ as its [C^N]$_2$Ir(Cl) (DMSO) derivative.

$^1$H-NMR (DMSO-d$^6$, 298K, 200 MHz, δ ppm) 3.16 (s, 6H), 3.19 (s, 6H), 5.35 (dd, J=2 and 8.7 Hz, 1H), 5.83 (dd, J=2 and 8.7 Hz, 1H), 6.70-7.00 (m, 4H), 7.37 (m, 2H), 8.86 (d, J=7 Hz, 1H), 9.21 (d, J=7 Hz, 1H).

Synthesis of [(2-(2,4-difluorophenyl)-4-dimethylaminopyridine)$_2$Ir(4-dimethylaminopyridine)-Cl]

[(2-(2,4-difluorophenyl)-4-dimethylaminopyridine)$_2$Ir Cl]$_2$ (195 mg, 0.139 mmol) and 4-dimethylaminopyridine (44 mg, 0.36 mmol) were refluxed in CH$_2$Cl$_2$ (100 ml) for 3 hours. After evaporation of the solvent, the yellow solid was dissolved in the minimum of CH$_2$Cl$_2$ and poured into Et$_2$O (150 ml). The yellow precipitate was filtered, washed with Et$_2$O and air dried to afford 290 mg (81%) of the desired complex as a yellow solid.

Synthesis of [(2-(2,4-difluorophenyl)-4-dimethylaminopyridine)$_2$Ir(4-dimethylaminopyridine)CN] (Complex (XIV))

[(2-(2,4-difluorophenyl)-4-dimethylaminopyridine)$_2$Ir(4-dimethylaminopyridine)Cl] (100 mg 0.122 mmol) and tetrabutylammoniumcyanide (42 mg, 0.156 mmol) were refluxed in CH$_2$Cl$_2$ (100 ml) for 3 hours. After evaporation of the solvent, the yellow solid was dissolved in the minimum of CH$_2$Cl$_2$ and precipitated with methanol (15 ml). The yellow precipitate was filtered, washed with Et$_2$O and air dried to afford 69 mg (70%) of the desired complex as a pale yellow solid.

Complex (XIV) was found to have a maximum emission at 468 nm, i.e. in the blue region (430-500 nm).

Figure 0002:
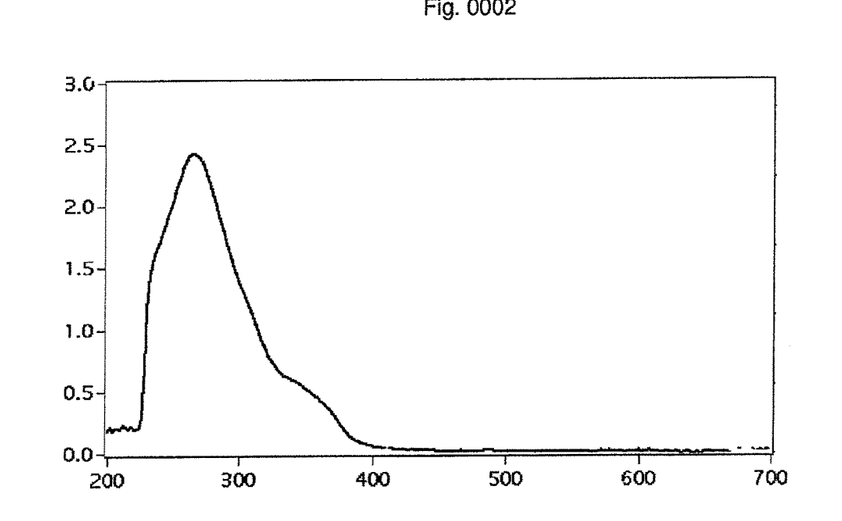

FIG. 0002 depicts the emission spectra registered from a complex (XIV) solution in dichloromethane at 273 K by excitation at 380 nm; the abscissa stand for the wavelength in nm and the ordinate stands for emission intensity (cps).

Figure 0003:
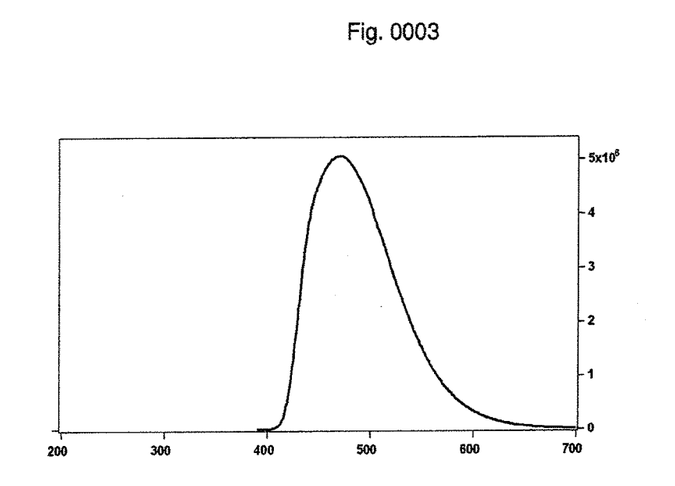

FIG. 0003 shows the adsorption spectra registered from a complex (XIV) solution in dichloromethane at 273 K; the abscissa stand for the wavelength in nm and the ordinate stands for adsorption (OD).

Synthesis of [(2-phenylpyridine)$_2$Ir(pyridine)Cl]

[(2-phenylpyridine)$_2$IrCl]$_2$ (100 mg, 0.093 mmol) and pyridine (16 ng 0.202 mmol) were refluxed in CH$_2$Cl$_2$ (100 ml) for 4 hours under argon. The solvent CH$_2$Cl$_2$ was evaporated, and the resulting yellow solid was dissolved in 1 mL of CH$_2$Cl$_2$. To this concentrated solution, 15 ml of Et$_2$O were added. The yellow precipitate was filtered, washed with Et$_2$O and air dried to afford 90 mg (yield 78%) of target complex.

Synthesis of [(2-phenylpyridine)$_2$Ir(pyridine)CN], (Comparative Complex XXIX)

((XXIX))

[(2-phenylpyridine)$_2$Ir(pyridine)Cl] (90 rye 0.143 mmol) and tetrabutylammoniumcyanide (45 mg, 0.168 mmol) were refluxed in 100 mL of CH$_2$Cl$_2$ for 3 hours. After evaporation of the solvent, the yellow solid was dissolved in the minimum of CH$_2$Cl$_2$, and precipitated with methanol (5 ml). The yellow precipitate was filtered, washed with Et$_2$O and air dried to afford 54 mg (61%) of the desired complex as a pale yellow solid.

Complex (XXIX) was found to have two peaks of emission when excited at 380 nm, a first at 490 nm and a second at 510 nm, with most of the emission intensity out of the blue region (430-500 nm).

Synthesis of [(2-(2,4-difluorophenyl)-4-dimethylaminopyridine)$_2$Ir(pyridine)Cl]

[(2-(2,4-difluorophenyl)-4-dimethylaminopyridine)$_2$Ir Cl]$_2$ (63 mg, 0.045 mmol) was dissolved in 80 mL of in CH$_2$Cl$_2$ under stirring. After 15 minutes, pyridine (8 mg 0.10 mmol) was dissolved in 1 ml of in CH$_2$Cl$_2$ and added to the dimer solution. The reaction mixture was refluxed for 6 hours. After evaporation of the solvent, the yellow solid was dissolved in 1 mL of CH$_2$Cl$_2$ and precipitated by addition of diethylether (10 ml). The yellow precipitate was filtered, washed with Et$_{20}$ and air dried to afford 50 mg (yield, 71%).

Synthesis of [(2-(2,4-difluorophenyl)-4-dimethylaminopyridine)$_2$Ir(pyridine)CN], (Complex XIX)

[(2-(2,4-difluorophenyl)-4-dimethylaminopyridine)$_2$Ir (pyridine)Cl] (50 mg, 0.065 mmol) was first dissolved in 80 mL of CH$_2$Cl$_2$ under argon. To this solution was added a solution of tetrabutylammoniumcyanide (20 mg 0.074 mmol) in 1 of CH$_2$Cl$_2$. The reaction mixture was refluxed for 3 hours. After evaporation of the solvent, the yellow solid was dissolved in a minimum amount of CH$_2$Cl$_2$ and precipitated with methanol (5 ml). The yellow precipitate was filtered, washed with Et$_2$O and air dried to afford 29 mg (yield, 59%) of the desired complex as a grey pale yellow solid.

Complex (XIX) was found to possess a peak of emission when excited at 380 nm in the blue region, with a shoulder at 457 nm and a main peak centred at 473 nm.

Figure 0004:
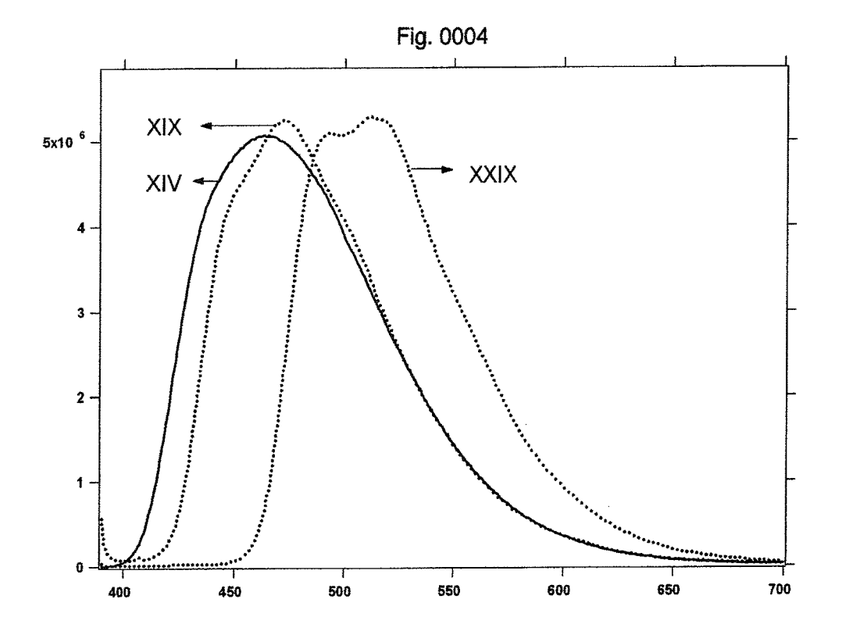

FIG. 0004 depicts the emission spectra registered from solutions of complex (XIV), complex (XIX) and comparative complex (XXIX) in dichloromethane at 273 K by excitation at 380 nm; the abscissa stand for the wavelength in nm and the ordinate stands for emission intensity (cps).

It sorts out from comparison between complexes (XIV), (XIX) and (XXIX) that only the inventive combination of the dialkylamino-substituted orthometalated ligands, of the monodentate neutral ligand (L) and of the monodentate anionic ligand (T) as above specified it is advantageously possible to obtain light emitting materials comprising [C^N]$_2$M(T)(L) complexes, having maximum emission between 430 nm and 500 nm, thus corresponding to a blue emission.

The invention claimed is:

1. A light emitting material comprising a neutral complex of formula (1):

(I)

wherein:

M represents a transition metal of atomic number of at least 40;

$E_1$ represents a non metallic atom group required to form a 5- or 6-membered aromatic or heteroaromatic ring, optionally condensed with additional aromatic moieties or non aromatic cycles, said ring optionally having one or more substituents, optionally forming condensed structure with the ring comprising $E_2$, said ring coordinating to the metal M via a $sp^2$ hybridized carbon;

$E_2$ represents a non metallic atom group required to form a 5- or 6-membered heteroaromatic ring, optionally condensed with additional aromatic moieties or non aromatic cycles, said ring optionally having one or more substituents, optionally forming a condensed structure with the ring comprising $E_1$, said ring coordinating to the metal M via a $sp^2$ hybridized nitrogen;

T is a monodentate anionic ligand chosen among cyanide (CN), thiocyanate (NCS) and cyanate (NCO);

L is a monodentate neutral ligand, coordinating to the metal M through a $sp^2$ or $sp^3$ hybridized nitrogen atom and selected from the structures represented by following formulae (III) to (VIII) or tautomers thereof:

(III)

(IV)

(V)

(VI)

(VII)

(VIII)

wherein:
J is a group chosen among the group consisting of —CH═CH—, N—H, N—$R^1$, O, S or Se;
G is a group chosen among the group consisting of —CR'═CR'—, —CH═N—, —CR'═N—;
Z is a substituent selected from the group consisting of halogens, $OR_0$; —$SR_0$; —$N(R_0)_2$; —$P(OR_0)_2$ and —$P(R_0)_2$; wherein $R_0$ is a $C_1$-$C_6$ alkyl, fluoro- or perfluoroalkyl group, e.g. —$CH_3$, -$nC_4H_9$, -$iC_3H_7$, —$CF_3$, —$C_2F_5$ or —$C_3F_7$ or a $C_1$-$C_6$ alkyl, fluoro- or perfluoroalkyl group having one or more ether groups, e.g. —$CH_2$—($CH_2$—O—$CH_2$)$_n$—$CH_3$, —$CH_2$—[$CH_2$($CH_3$)—O—$CH_2$]$_n$—$CH_3$, —($CF_2$O)$_n$—$C_2F_5$, with n being an integer from 1 to 8;

R', R*, R¤, the same or different each other at each occurrence, represent F, C, Br, $NO_2$, CN, a straight-chain or branched or cyclic alkyl or alkoxy group having from 1 to 20 carbon atoms, in each of which one or more non-adjacent —$CH_2$— groups may be replaced by —O—, —S—, —$NR^1$, or —$CONR^2$—, and in each of which one or more hydrogen atoms may be replaced by F; or an aryl or heteroaryl group having from 4 to 14 carbon atoms which may be substituted by one or more non aromatic radicals; and a plurality of substituents R', R*, or R¤, either on the same ring or on the two different rings, may in turn together form a further mono- or polycyclic ring system, optionally aromatic;

R", $R^1$, $R^2$, the same or different at each occurrence, are each H or an aliphatic or aromatic hydrocarbon radical having from 1 to 20 carbon atoms;

d is an integer from 0 to 3;
c is an integer from 1 to 3;
$R^x$ and $R^y$ equal or different at each occurrence, are independently chosen among $C_1$-$C_6$ alkyl, fluoro- or perfluoroalkyl groups, e.g. —$CH_3$, -$nC_4H_9$, -$iC_3H_7$, $CF_3$, —$C_2F_5$, —$C_3F_7$ or $C_1$-$C_6$ alkyl, fluoro- or perfluoroalkyl groups having one or more ether groups; preferably $R^x$ and $R^y$ are independently chosen among $C_1$-$C_6$ alkyl groups;
w is an integer of from 1 to 4.

2. The light emitting material of claim 1, comprising a neutral complex of formula (II):

(II)

wherein:
$R_x$, $R_y$, w, L and T have the same meaning as above defined;
X is a group chosen among the group consisting of —CH═CH—, N—H, N—$R^1$, O, S or Se;
Y is a group chosen among the group consisting of —CH═CH—, N—H, N—$R^1$, P, S or Se;
$R^1$, the same or different at each occurrence, is independently an aliphatic or aromatic hydrocarbon radical having from 1 to 20 carbon atoms;
$R_A$ and $R_B$, equal or different each other and at each occurrence are independently selected among —F, —Cl, —Br, —NO$_2$, —CN; a straight-chain or branched or cyclic alkyl or alkoxy group having from 1 to 20 carbon atoms, in each of which one or more nonadjacent —CH$_2$— groups may be replaced by —O—, S—, —NR$^1$—, or —CONR$^2$—, and in each of which one or more hydrogen atoms may be replaced by F; an aryl or heteroaryl group having from 4 to 14 carbon atoms which may be substituted by one or more nonaromatic radicals; and a plurality of substituents R$_A$ and/or R$_B$, either on the same ring or on the two different rings, may in turn together form a further mono- or polycyclic ring system, optionally aromatic;

a is an integer from 0 to 4;

b is an integer from 0 to 4.

3. The light emitting material according to claim 2 comprising a neutral complex of formula (XI) here below:

(XI)

wherein:

T, Y, X, G, R$_A$, R$_B$, R$^X$, R$^Y$, a, b, and w have the same meaning as above defined, and w' is an integer of from 1 to 3.

4. The light emitting material according to claim 3 comprising a neutral complex of formula (XII):

(XII)

wherein:

R$^x$, R$^Y$, w and w' have the same meaning as above defined;

R$_M$, equal or different at each occurrence, is independently selected from —F and alkoxy group having from 1 to 20 carbon atoms; and m is an integer between 1 and 4, preferably between 1 and 3.

5. The light emitting material according to claim 1, comprising a neutral complex of formula (XIV):

(XIV)

6. A method for using the light emitting material according to claim 1 in the emitting layer of an organic light emitting device.

7. The light emitting material according to claim 1 used as a dopant in a host layer, wherein the dopant functions as an emissive layer in an organic light emitting device.

8. An organic light emitting device (OLED) comprising an emissive layer (EML), said emissive layer comprising the light emitting material according to claim 1, optionally with a host material.

9. A light emitting material comprising a neutral complex of formula (XIV):

(XIV)

10. The light emitting material of claim 1, wherein L is selected from the structures represented by the following formulae (III) to (VII) or tautomers thereof:

(III)

(IV)

(V)

(VI)

(VII)

11. The light emitting material of claim 1, wherein the neutral complex is selected from the formula XIII to XVII:

(XIII)

(XIV)

(XV)

(XVI)

(XVII)

12. The light emitting material in accordance with claim 1 wherein M is Ir.

13. The light emitting material in accordance with claim 1 wherein T is a cyanide.

14. The light emitting material in accordance with claim 1 wherein L is coordinating to the metal M through a $sp^2$ hybridized nitrogen atom.

15. The light emitting material in accordance with claim 1 wherein $R^x$ and $R^y$ are chosen among $C_1$-$C_6$ alkyl groups.

16. The light emitting material in accordance with claim 2 wherein X is —CH=CH—.

17. The light emitting material in accordance with claim 2 wherein Y is —CH=CH—.

* * * * *